US010286278B1

(12) United States Patent
Ahmed

(10) Patent No.: US 10,286,278 B1
(45) Date of Patent: May 14, 2019

(54) WEARABLE ATHLETIC PERFORMANCE MONITORING DEVICE

(71) Applicant: Abdullah Ahmed, Islamabad (PK)

(72) Inventor: Abdullah Ahmed, Islamabad (PK)

( * ) Notice: Subject to any disclaimer, the term of this patent is extended or adjusted under 35 U.S.C. 154(b) by 0 days.

(21) Appl. No.: 15/625,816

(22) Filed: Jun. 16, 2017

(51) Int. Cl.
| | |
|---|---|
| A63B 69/36 | (2006.01) |
| A63B 69/00 | (2006.01) |
| A63B 24/00 | (2006.01) |
| A63B 71/06 | (2006.01) |

(52) U.S. Cl.
CPC ...... *A63B 69/0015* (2013.01); *A63B 24/0062* (2013.01); *A63B 71/0622* (2013.01); *A63B 2071/0694* (2013.01); *A63B 2209/10* (2013.01); *A63B 2220/40* (2013.01); *A63B 2220/803* (2013.01); *A63B 2220/836* (2013.01); *A63B 2225/50* (2013.01)

(58) Field of Classification Search
USPC ....... 473/199, 207, 209, 215, 221, 266, 409, 473/458
See application file for complete search history.

(56) References Cited

U.S. PATENT DOCUMENTS

| | | | | |
|---|---|---|---|---|
| 5,980,472 A | * | 11/1999 | Seyl | A61B 5/1121 600/587 |
| 6,275,996 B1 | * | 8/2001 | Redwood | A41D 19/0024 2/160 |
| 6,890,285 B2 | * | 5/2005 | Rahman | A61B 5/4833 482/4 |
| 7,033,281 B2 | * | 4/2006 | Carnahan | A61B 5/1071 434/247 |
| 7,981,057 B2 | * | 7/2011 | Stewart | A41D 13/02 600/587 |
| 8,025,632 B2 | * | 9/2011 | Einarsson | A41D 13/1281 602/23 |
| 8,784,342 B2 | * | 7/2014 | Hyde | A61B 5/103 600/587 |
| 9,078,478 B2 | * | 7/2015 | Ross, Jr. | A41D 27/10 |
| 9,582,072 B2 | * | 2/2017 | Connor | G06F 3/011 |
| 2009/0088674 A1 | * | 4/2009 | Caillouette | A61B 5/1071 602/26 |
| 2009/0204031 A1 | * | 8/2009 | McNames | A61B 5/1071 600/595 |
| 2014/0375470 A1 | * | 12/2014 | Malveaux | A61B 5/0015 340/870.01 |

(Continued)

*Primary Examiner* — Nini Legesse
(74) *Attorney, Agent, or Firm* — Bajwa IP Law Firm; Haris Zaheer Bajwa

(57) ABSTRACT

The present disclosure relates to an athletic performance monitoring device that could be worn over a limb of an athlete for assessing the motions of the limb. The device comprises of a flexible sleeve that could be worn around the limb; an elongated flexible member that can be mounted over the flexible sleeve and multiple motion sensors embedded at appropriate positions over the elongated flexible member for sensing the motions of the limb. The device is particularly useful in the sport of cricket wherein the device could be mounted over the bowling arm of the bowler for differentiating between the illegal and legal bowling action by assessing the kinematics of the elbow joint during the latter stages of ball delivery. Further the device may be configured for monitoring the arm force, action time, and twist in the bowler's arm just before the ball is released in the course of ball delivery.

13 Claims, 5 Drawing Sheets

(56) References Cited

U.S. PATENT DOCUMENTS

| | | | |
|---|---|---|---|
| 2015/0279231 A1* | 10/2015 | Kuo | G09B 19/003 |
| | | | 702/19 |
| 2015/0351690 A1* | 12/2015 | Toth | A61B 5/6833 |
| | | | 600/373 |
| 2015/0366504 A1* | 12/2015 | Connor | A61B 5/6804 |
| | | | 600/301 |
| 2016/0338621 A1* | 11/2016 | Kanchan | A61B 5/0022 |

* cited by examiner

WEARABLE ATHLETIC PERFORMANCE MONITORING DEVICE

FIELD OF INVENTION

The present disclosure relates to a wearable athlete performance monitoring device, more particularly the present disclosure relates to a device having one or more motion sensors that can be worn over a limb of an athlete for biomechanical assessment of the motions of the limb.

BACKGROUND

Athletes engage in different kind of sports and compete with each other for entertainment. The competition encourages the athletes to continuously hone their athletic skills by training, wherein the athletes employ the services of trained professionals/coaches, or may undergo self-training. The major purpose of both coaching and self-training is to overcome bad habits and learn correct techniques of a particular sport. Different sports require different skill sets, for example, sports like cricket, basketball, baseball, tennis and the like require particular coordination in the movement of upper limbs.

In cricket, certain bowling actions by the bowler in course of ball delivery are undesired and are commonly referred to as "throwing" or "chucking". Throwing is said to occur when during the bowling action, the bowler during the latter stage of a ball delivery, just before the release of ball, extends the bowling arm beyond a permissible threshold. During the latter stage of the ball delivery, only the rotation of the shoulder or wrist movement is desired to impart velocity to the ball not the elbow. The general bodies governing the sport of cricket have made the throw-like bowling action illegal and one of such general body, International Cricket Council (ICC), has set the permissible threshold of 15 degrees of extending the bowling arm for all bowlers.

To differentiate between the illegal bowling and the legal bowling actions, the change in the elbow angle must be measured during the latter stage of the ball delivery, from the bowling stage when the upper bowling arm reaches the level of the shoulder height and is parallel to the ground, referred herein as the "start of action," (SOA) to the stage at which the ball is released from the hand of the bowler, this stage is referred herein as "ball release" stage. Some threshold, such as, fifteen degrees in the change of elbow angle is tolerated to allow natural flexing of the elbow joint during the course of legal ball delivery. The bowler is however completely allowed for flexing or rotating the wrist during the normal course of ball delivery.

The athletes may intentionally extend their arm during latter stage of ball delivery for adding excess pace to the ball, or an athlete may have naturally developed bad habits during the training. Thus, the supervision of a coach becomes essential for avoiding such bad habits and learning the correct techniques of bowling and further honing the skills for improving the athletic performance. However, such professional services of the coach may not be available or are very expensive. Moreover, while training in a group, the coach may not have enough time to closely supervise each trainee. Even in the presence of a coach, such extension may not be detectable via a naked eye. In the absence of proper coaching, the trainee may develop wrong techniques. Thus, a need exists for a device that may allow monitoring the motion of the arm including the change in elbow angles, and provides feedback about the bowling action. Presently, biomechanics labs are used to assess the illegal bowling actions of athletes. Such labs are expensive, complex, and are not easily accessible.

Thus, there is a need for a portable device that may monitor the arm movements of a bowler during the bowling action in cricket. Such device would allow a bowler to self-monitor their training regimes and allow coaches or umpires to detect illegal bowling action during the training or a competition.

SUMMARY OF THE INVENTION

It is, therefore, a principal objective of an exemplary embodiment of the present disclosure to provide a wearable athlete performance monitoring device that could be worn around the bowling arm of the bowler in the cricket sport for biomechanical assessment of the bowling arm during the course of ball delivery.

Another exemplary embodiment of the present disclosure comprises one or more sensors to calculate changes in angle of the elbow joint during the latter stages of ball delivery.

According to another exemplary embodiment of the present disclosure, the device may provide feedback to the athlete in near real time or latter about the bowling performance.

According to another exemplary embodiment of the present disclosure, the device may allow self-training of the athlete by providing warning to the athlete in near real time about bad or undesired techniques of bowling actions.

Still according to another exemplary embodiment of the present disclosure, the device may allow a coach or an umpire to detect an illegal bowling action during the course of ball delivery.

According to another exemplary embodiment of the present disclosure, the device may be compact, light in weight and economic to manufacture.

Certain exemplary embodiments of the present disclosure may provide a wearable athletic performance monitoring device that may be worn over a limb of an athlete for assessing the motions of a limb. The wearable device may comprise a flexible sleeve made of stretchable textile material that may be adapted to be worn around an exemplary limb of the athlete, an elongated flexible member, made of similar or different textile material, having a proximal end and a distal end, that may be mounted over the flexible sleeve. Multiple coupling members such as a Velcro, may be provided on the inner side of the elongated flexible member for removably mounting the elongated flexible member over the flexible sleeve. The elongated flexible member may have markings for properly positioning the elongated flexible member over the limb. The device further comprises multiple motion sensors and a flex sensor embedded at appropriate positions in the elongated flexible member and the sensors may be configured to assess different motions of the arm. Further the device may comprise a processing unit for processing the sensor data generated from one or more of the sensors and generating the processed data. The processing unit may comprise a memory for storing the processed data for later retrieval and analysis. The processing unit may further comprise a transmitter for sending the processed data to an external computing device, such as a smart phone for further processing and analysis.

In an exemplary embodiment, the wearable athletic performance monitoring device consistent with the present disclosure may be adapted to be worn over an arm of the bowler in the cricket sport for assessing the motions of the arm during the course of ball delivery. The device may comprise one or more sensors selected from inertial sensors, accelerometers, gyroscopes, Flex sensor or a combination thereof, wherein the sensors are configured in the elongated flexible member for assessing the change in elbow angle for detecting illegal bowling action, and further monitoring the twist of arm assessing the bowling performance of the athlete. The device may further monitor action time and arm force through certain movements.

BRIEF DESCRIPTION OF THE EMBODIMENTS

The accompanying figures, which are incorporated herein, form part of the specification and illustrate exemplary embodiments of the present disclosure. Together with the description, the figures further serve to explain the principles of and to enable a person skilled in the relevant arts to make and use the exemplary embodiments of the present disclosure.

DETAILED DESCRIPTION

The present disclosure relates to an athletic performance monitoring device that may be worn over a limb of an athlete and the device includes one or more sensors for near real-time biomechanical assessment of the motions of the limb. Such biomechanical assessment of the limb may be used to quantify bad habits or illegal moves of the limb during an event of training or competition. The limb may be an arm or leg of the athlete and the athletic performance monitoring device may be worn in one or both of the arms or legs. The athletic performance monitoring device according to an exemplary embodiment may, with no modifications or with minor modifications, may be used in different sports that involves coordinated movement of arm or leg, such as, cricket, baseball, tennis, and the like. Exemplary embodiments consistent with the present disclosure are described primarily in the context of cricket, more particularly for a bowling action in cricket.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Figure 1:
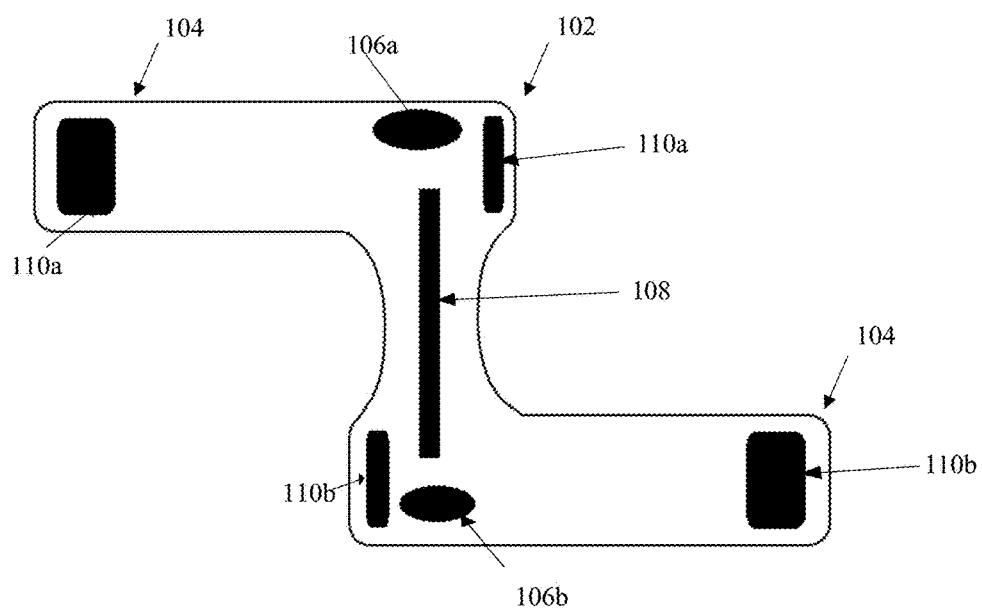
FIG. 1 is a planar view of the inner side of the elongated flexible member, consistent with exemplary embodiments of the present disclosure.
Figure 2:
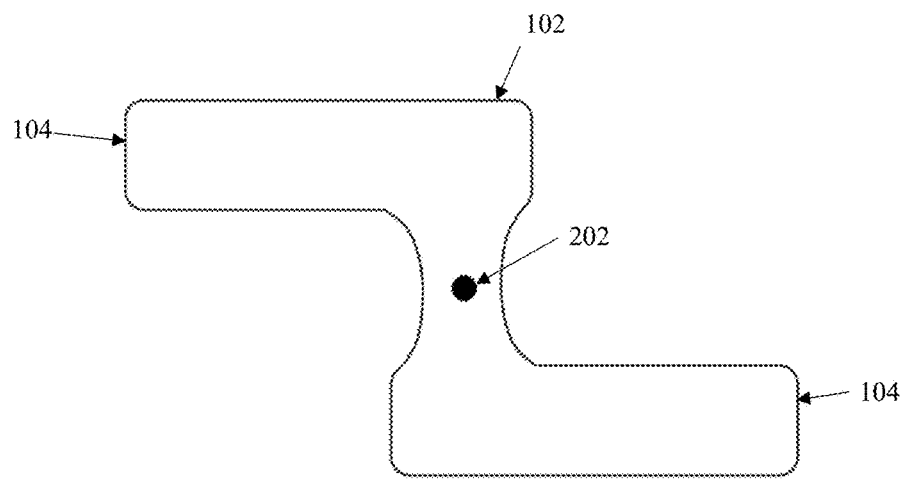
FIG. 2 is a planar view of outer side of the elongated flexible member of FIG. 1.
Figure 3:
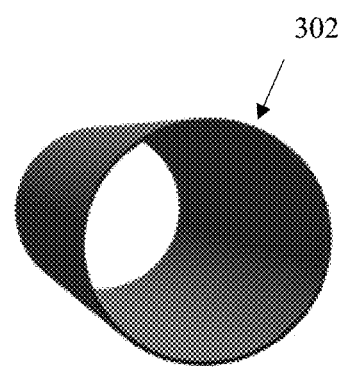
FIG. 3 is a front and side perspective view of the flexible sleeve, consistent with exemplary embodiments of the present disclosure.

Now referring to the drawing, FIGS. 1-5 illustrate exemplary embodiments of the athletic performance monitoring device, consistent with the present disclosure. FIGS. 1 and 2 show the inner side and outer side of an exemplary elongated flexible member respectively and FIG. 3 illustrates a flexible sleeve. The athletic performance monitoring device consistent with exemplary embodiments of the present disclosure includes an elongated flexible member 102 having a pair of straps 104 extending in opposite directions and perpendicularly to the elongated flexible member, multiple motion sensors 106 and 108 embedded in the elongated flexible member, a flexible sleeve 302, a processing unit and a power module.

Exemplary flexible sleeve may be a cylindrical stretchable garment that may be worn over the bowling arm wherein the bowler may insert the arm through one of the opening of the sleeve and drag the sleeve upwards. In an exemplary embodiment, the flexible sleeve may have a larger diameter at the posterior and a smaller diameter at the front, where the front refers to part of the sleeve that is closest to a bowler's hand as opposed to their shoulder when the sleeve is worn by the bowler. The sleeve covers the portion of the forearm and extends upwards up to the upper arm passing through the elbow joint. The sleeve is retained firmly over the arm due to stretch of the sleeve. The sleeve may be made of suitable textile material that is skin friendly, light in weight, breathable, and flexible so that to ensure agility while elbow movement. The sleeve may be preferably made of Lycra material that is washable. However, additional materials that are stretchable materials may be utilized. In exemplary embodiments, the sleeve may provide additional support, strength, and comfort to a bowler's arm. Additionally, it may vary in sizes and volume correlating to arm sizes of bowlers.

The elongated flexible member having the proximal end and a distal end may be adapted to mount over the sleeve. The length of the elongated flexible member may be such that when mounted over the sleeve, the proximal end of the elongated flexible member may face the forearm and the distal end may cover a portion of the upper arm. The length of the elongated flexible member may be in the range of 8-12 inches. In additional embodiments, the length and other dimensions of the elongated flexible member may be customized according to a user, for example, users with longer arms may require lengthier sleeves and elongated flexible members and vice versa. The elongated flexible member may be provided with suitable markings to allow the elongated flexible member to be properly mounted over the sleeve, for example, as shown in FIG. 2, a dot 202 is provided as the marking. The dot may be positioned such that when the elongated flexible member is mounted over the bowling arm, the dot overlies the elbow joint. The elongated flexible member and the pair of straps may be made in a single piece, or the pair of straps could be coupled to the elongated flexible member through sewing, adhesive, or an additional method for connecting two pieces. The elongated flexible member and straps may be made of a material that allows embedding electronic device and further provides protection to the electronic devices and proper insulation for preventing a shock. In exemplary embodiments, the elongated flexible member and straps may be made of neoprene that is flexible so that to ensure agility while elbow movement and may be easily cleaned off the dust. The inner side of the elongated flexible member as shown in FIG. 1 may further include multiple number of coupling members 110a and 110b that may allow removably mounting the elongated flexible member. The coupling member may be Velcro, however, other suitable coupling members such as buttons or zips may also be utilized, in addition to direct attachment by stitching, etc. Moreover, if required, the sleeve may also be provided with other engaging portion of the coupling member. The elongated flexible member may be removed from the sleeve and the sleeve may be washed as and when required.

Figure 4:
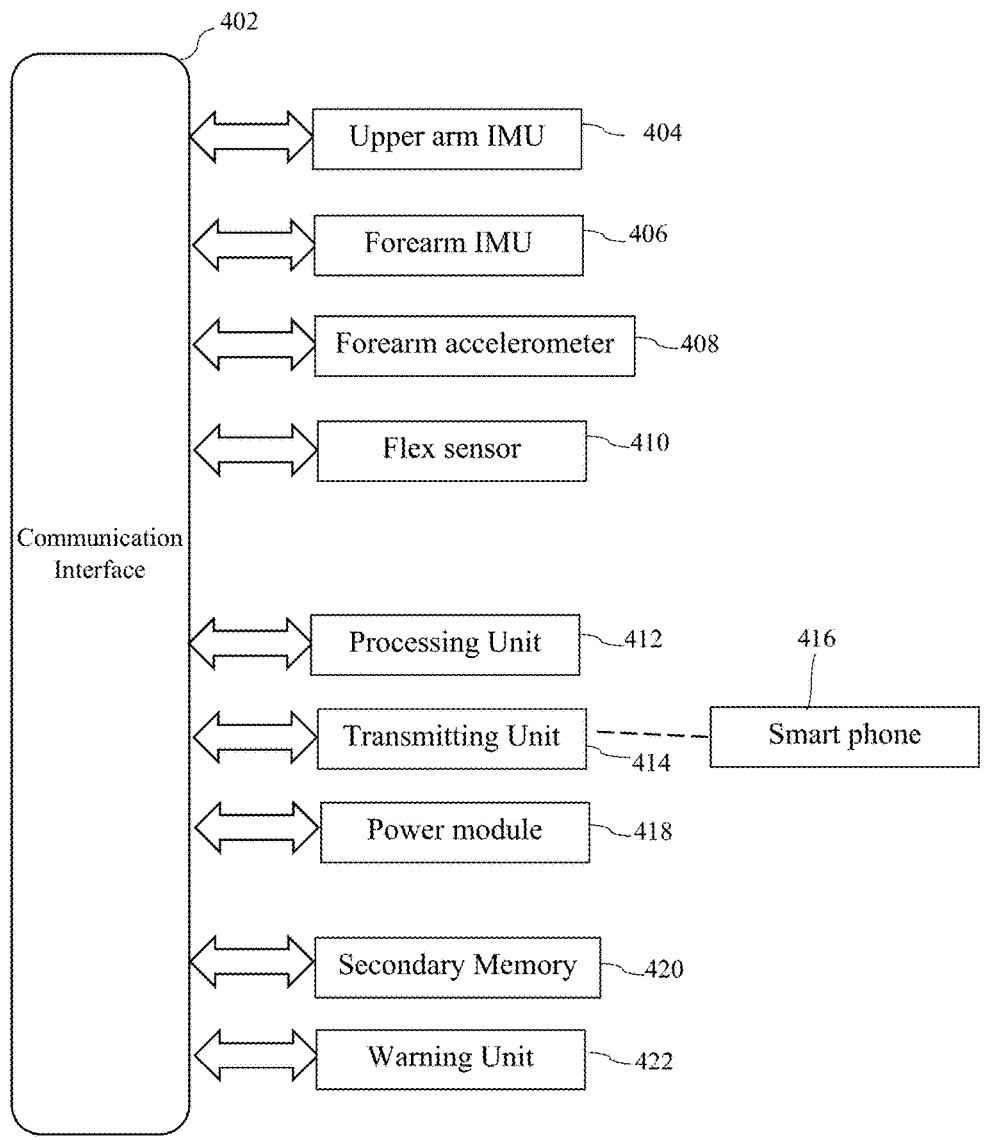
FIG. 4 is a block diagram illustrating electronic components in the device, consistent with exemplary embodiments of the present disclosure.

FIG. 4 illustrates electronic components of the wearable device, an exemplary embodiment consistent with the present disclosure. An electrical communication interface 402 allows for communication in various components. In exemplary embodiments, there are multiple motion sensors for assessing the biomechanics of the bowling arm. The motion sensors may be embedded at suitable positions, such as 106 and 108 of FIG. 1, in the elongated flexible member to allow for detection of different motions of the bowling arm in the course of ball delivery. In embodiments, motion sensors that may be used include inertial sensors, for example, IMU (inertial measurement unit). The IMU may be a combination of accelerometer and a gyroscope that measures and reports a body's specific force and angular rate. Now, to differentiate between the desired and un-desired bowling action, a change in the elbow angle from "start of action", that is, when during the later stage of ball delivery, the arm is parallel to the ground to the "ball release" action is important. To identify the "start of action" stage, the IMU 404 may be embedded near the distal end of the elongated flexible member, that is, towards the upper arm. The IMU may be configured to have one of the axis align with the arm, for example, the Y axis may be in line with the arm, so that the Z axis points towards gravity when the arm is parallel to the ground. The processing unit 412 may be electrically coupled to the inertial sensor for receiving the data/signals generated by the sensors, referred herein as sensor data. The processing unit may receive the sensor data and process it according to one or more algorithms to generate the output data. For example, the sensor data from both the accelerometer and gyroscope units of the IMU may be fused using fusion algorithms like a complimentary filter or Kalman filter and the fused data may then used to measure gravity accurately. The assembly and functioning of the electronic processing devices, such as computing units and micro-controllers, including the hardware and software, may be utilized for processing signals from the motion sensors. The processing unit may be embedded in the elongated flexible member and preferably the processing unit is embedded near the distal end. The processing unit may be connected to the sensors and any other electronic component through flexible wiring 402 that may also be embedded in the elongated flexible member and the electrical wires may be embedded on the inner side of the elongated flexible member. The electrical components of the device may be powered by a portable battery 418 which may be connected to the electrical components through the flexible wires embedded in the elongated flexible member. The battery may also be disposed near the distal end of the elongated flexible member, that is, towards the upper arm, along with the processing unit.

Next to identify the "ball release" action, another IMU 406 may be embedded near the proximal end of the elongated flexible member, that is, at the forearm. The configuration of the sensors at proximal end differs from the sensors at the distal end by removing the gravity measurement wherein the IMU may be configured to measure the arm force. The ball release action may be identified by change in acceleration of arm, that is, once, the bowler is about to release the ball, the bowler arm is in acceleration mode and once the ball leaves the hand, there is a deceleration mode with the acceleration falling down to a zero value. Furthermore, an additional three axis 100 g accelerometer 408 may be placed with the proximal end IMU to accurately capture the bowler's arm force. Moreover, during the bowling activity, the hand moves in such a way that it forms a circle and the force thus acts always towards the center of the circle, thus producing the max acceleration in just one axis of the accelerometer whereas the other two axis don't face a lot of acceleration, this makes the accelerometer prone to saturation in that one particular axis e.g. if the 3 axis accelerometer can measure 100 g in all x, y & z but faces 120 g in y and 0 g in x & z, then the sensor would have saturated. So, to avoid this situation the accelerometer may be mounted in a way that the acceleration may equally distributed amongst all the three axis thus making it capable of measuring 173 g acceleration overall. The sensor data may be processed by the processing unit using suitable algorithms, for example, the sensor data from the forearm 100 g accelerometer that gives the raw acceleration value and the IMU that gives the quaternions, may be converted to gravity and the gravity is then removed from the raw acceleration to give linear acceleration. This linear acceleration may be obtained from all the three axes. The linear acceleration of the system may then be obtained by taking the root mean square of all the axes.

Next, to measure the elbow angles, a commercially available flex sensor 410 also known as a bend sensor may be deployed. The flex sensor may contain a substrate of variable resistive ink whose resistance increases with the unidirectional bend angle of the strip with a tolerance of 1°. So, the sensor may output values proportional to the change in resistance that can be converted to the change in elbow angle. The flex sensors may have to be calibrated for each user, as the different users may have different arm sizes and thus the sensor output may vary from user to user. The calibration may be done by keeping the arm completely straight and then at any another known angle, such as 45 degrees, where the device may then automatically map the rest of angle values. As shown in FIG. 1, the flex sensor 108 may be stitched on the inner side of the elongated flexible member and preferably from one side only, providing it space for bending on the other side, thereby, protecting it from permanent deformation. The position of the flex sensor is critical as it needs to be carefully placed at the elbow with the mid-point of the flex sensor strip aligning with the elbow joint. Once the device is worn with the flex sensor carefully placed on the elbow, twisting the arm in this situation both clockwise and anticlockwise can produce some error in the angle value. This is catered by another calibration process where after the angle calibration is done, the user twists the arm as much as he can in clockwise and anticlockwise directions, and from that the error in angle is mapped against the amount of twist which is then compensated for in real time with the changing arm twist. Alternatively, the elbow angles may be obtained from the two exemplary IMUs, that is, proximal end IMU and distal end IMU, wherein each IMU will give the gravity vectors and using the relative difference in between the gravity vectors of the two IMUs, the elbow angle may be determined.

An exemplary device may be used to determine the action time and arm twist. Basically once the bowler has finished a run up and is about to deliver the ball, his bowling hand starts to accelerate and this time period during which the acceleration takes place may be stamped as the action time. For any arm twisting, using the gyroscope on the forearm, the twist in the bowler's arm produced by the bowler when delivering the ball may be quantified. Typically, the angular velocity obtained from the gyroscope in rad/sec may be integrated to determine the twist about a certain axis in radian or in degrees. So, to find the arm twist, the axis which is parallel to the arm center axis may be chosen and the degree of twist about that axis may be calculated. In an exemplary embodiment, the change in the arm twist may be monitored in a time span comprising ten samples before the release point as the twist in the arm just before the release of ball is what has the most impact in producing the revolutions on the ball.

The processing unit may further include a memory 420 for storing data that may be retrieved or analyzed later, or the data may be sent directly to an external computing device 416. To send the data, the processing unit further includes a transmitting unit 414 electrically coupled to the processing unit for receiving the data and the power module 418. The transmitting unit may send the data in near real time to the external computing device, where further processing and analysis of the data may be done and the report generated that may be viewed on the display screen of the external computing device. In exemplary embodiments, the report may be displayed locally via an LCD or via LED displays or lights that may be embedded into the sleeve. The report may be generated in field and in near real-time of the training or sport event, or the data may be stored for later analysis. The transmitting unit may be connected to an external computing device through a port, such as, a USB port, or it may be wirelessly connected using wireless communication, such as Wi-Fi or a Bluetooth. The external computing device may be any computing device obvious to a skilled person, such as, a laptop, tablet computer, or a smart phone. The device of present invention may further include an alarm module, such as a beep alarm to notify the athlete in near real-time about an illegal move during training.

Figure 5:
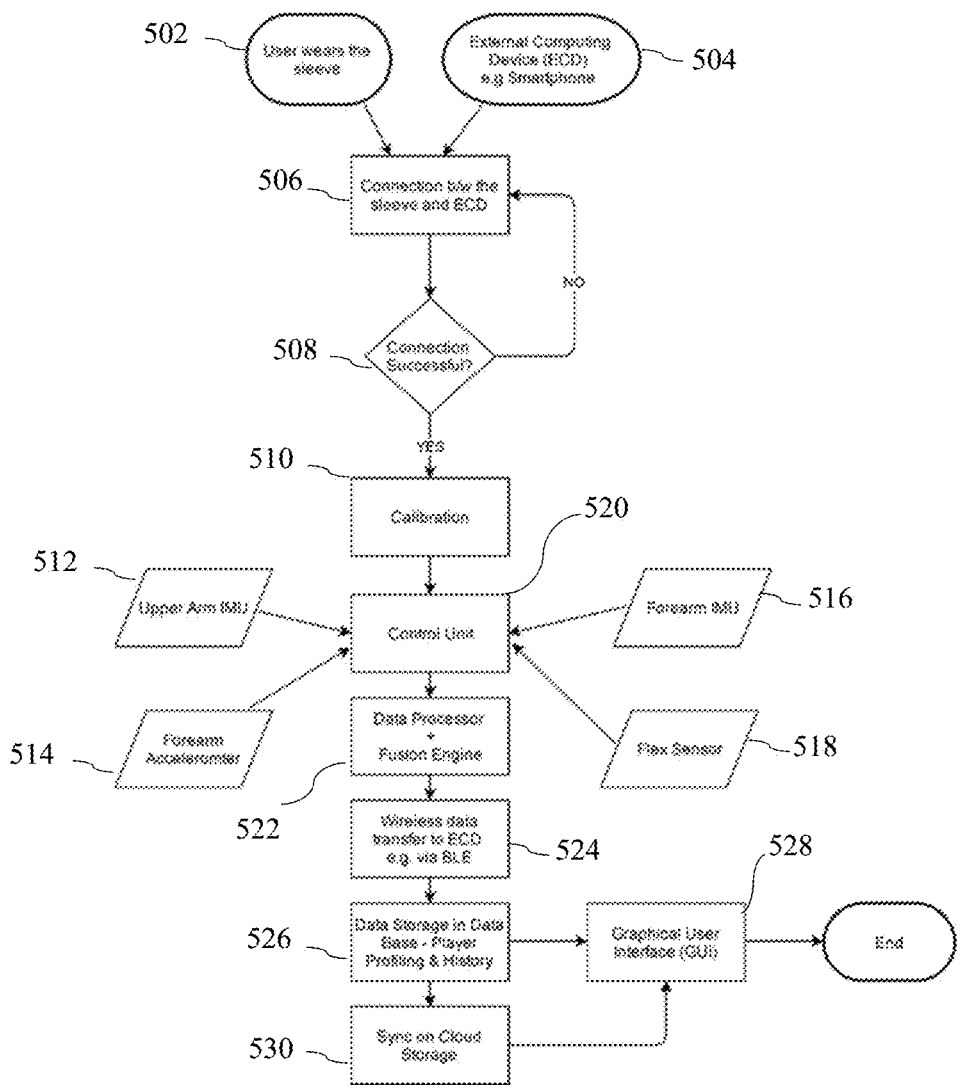
FIG. 5 is a flow diagram illustrating steps of an exemplary method, consistent with exemplary embodiments of the present disclosure.

FIG. 5 illustrates various steps of an exemplary method, consistent with exemplar embodiments of the present disclosure, for differentiating between legal and illegal bowling action of the bowler in cricket. The method may include step 502 of bowler wearing the flexible sleeve on his bowling arm and mounting the elongated flexible member over the sleeve such that the white dot on the outer surface of the sleeve overlies the elbow joint. Thereafter, the user (bowler) may initiate the step 504 for starting the app that is included in a computing device, such as, a smartphone. The smart phone may include software for detecting and pairing with exemplary wearable device. Step 506 may include detecting and pairing the smart phone with the exemplary wearable device. When the pairing is successful, the user may perform step 510 for calibrating the device. This step has to be performed first time to calibrate the device according to a specific user.

Thereafter, to detect the movement of the arm, motion sensors sense different movements, in step 512, the upper arm IMU detects the "start of action" stage and in step 514 and 516, the "ball release" stage and twist of the arm may be determined. Further a step 518 detects the movement of the elbow joint between "start of the action" and "ball release" stages. The step 520 includes receiving the sensor data generated in each step of 512, 514, 516 and 518. Thereafter, step 520 includes various processing algorithms performed by the processing unit to distinguish between legal and illegal bowling action, and further providing other performance parameters such as twist of the arm, arm force, and action time.

In order to detect the complete illegal action, the linear acceleration from the forearm may be constantly monitored, if the values are below a certain threshold level, they are discarded. If the value goes above that level then the system stores the current value and monitors the next value. Now, if the next value is greater than the previous one, then both values are stored in an array and the same process is continued. If the subsequent values are constantly higher than the previous ones, then another threshold is being monitored. If this latter threshold is now crossed then it is certain that the ball has been delivered. All the values stored in the array are then analyzed to find the global maxima, which is called the release point. A timer based interrupt continuously runs to read the flex sensor values to get the angle values throughout this process and these are also being stored in an array. Simultaneously, the upper arm IMU is being read to get the quaternions being converted to gravity to get the SOA. Ultimately, the maximum flex value and the flex value at release are found to get the arm extension.

The processed data from step 522, is transmitted by the transmitting unit to the smartphone in step 524 through Bluetooth, however, any other suitable communication such as Wi-Fi or infrared may also be used. The transmitting unit may include a BLE (Bluetooth low energy) chipset for pairing with the smartphone using Bluetooth and transmitting data. Thereafter, the step 526 includes indexing and storing of the received data in an exemplary database. The data may be indexed according to the selected user profile in the app, wherein such user profiles may be created in the app. Step 528 entails analyzing the indexed data in the database for the desired user, and displaying different performance parameters on the display screen of the computing device, like the smartphone. Step 530 may entail syncing the database with an external storage such as cloud storage from where the user data can be retrieved as and when required.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is to be claimed is:

1. A wearable device for assessing motions of a bowling arm of an athlete in a cricket sport, said wearable device comprising:

an elongated flexible member having a proximal end, a distal end, an inner side and an outer side, said elongated flexible member adapted to be mounted over said bowling arm, wherein said proximal end of the elongated flexible member faces the forearm and said distal end of the elongated flexible member extends up to the upper arm passing over the elbow joint;
a plurality of motion sensors consisting of an accelerometer, a first inertial sensor, a second inertial sensor, and a flex sensor embedded in said elongated flexible member, wherein the accelerometer and the first inertial sensor is embedded near said proximal end of the elongated flexible member and the second inertial sensor is embedded near said distal end of the elongated flexible member, and the flex sensor embedded in said elongated flexible member extending from near said proximal end of the elongated flexible member up to near said distal end of the elongated flexible member between the second inertial sensor and the combination of the first accelerometer and the first inertial sensor;
a processing unit in electrical communication with said plurality of motion sensor and said flex sensor, said processing unit configured for receiving and processing a plurality of sensor data generated from said plurality of motion sensor and said flex sensor and generating a processed data;
a transmitting unit operably coupled to said processing unit for receiving said processed data and transmitting said processed data to an external computing device; and
a power module to power said plurality of sensor, said processing unit, and said transmitting unit.

2. The wearable device according to claim 1, wherein said wearable device further comprises a flexible sleeve adapted to be worn over said bowling arm, and said elongated flexible member is mounted over said flexible sleeve.

3. The wearable device according to claim 1, wherein said elongated flexible member is made of neoprene.

4. The wearable device according to claim 1, wherein length of said flexible member is between the ranges of 8-12 inches.

5. The wearable device according to claim 1, wherein the second inertial sensor configured to have one axis aligned with said bowling arm.

6. The wearable device according to claim 1, wherein the outer side of said elongated flexible member is provided with a marking for positioning said elongated flexible member over said mounting arm.

7. The wearable device according to claim 6, wherein said marking is a dot, said dot is positioned such that when the elongated member is mounted over said bowling arm, said dot overlies the elbow joint.

8. The wearable device according to claim 1, wherein said power module is a rechargeable battery.

9. The wearable device according to claim 1, wherein said power module, said processing unit, and said transmitting unit are disposed near the distal end of said elongated flexible member.

10. The wearable device according to claim 1, wherein said plurality of motion sensor and said flex sensor is configured for detecting a change in angle motion of the elbow joint.

11. The wearable device according to claim 1, wherein said plurality of motion sensors is configured for detecting a twist motion of the forearm and the wrist.

12. The wearable device according to claim 1, wherein said external computing device is a smart phone.

13. A method of assessing an illegal bowling action of a bowler in a cricket sport, said method comprising the steps of:
providing a flexible sleeve made of textile material, said flexible sleeve adapted to be worn around said bowling arm, said sleeve extends from the forearm to the upper arm passing over the elbow joint;
providing an elongated flexible member made of textile material and having a proximal end and a distal end, said elongated flexible member adapted to be removably mount over said flexible sleeve, said proximal end of the elongated flexible member faces the forearm and said distal end extending up to the upper arm;
providing a plurality of coupling members over said elongated flexible member for removably mounting said elongated flexible member over said flexible sleeve;
disposing a plurality of motion sensors consisting of an accelerometer, a first inertial sensor, a second inertial sensor, and a flex sensor, wherein the disposing a plurality of motions sensors comprises:
disposing the second inertial sensor near said distal end of the elongated flexible member, configuring said inertial member to have one axis align with said bowling arm;
disposing the first inertial sensor and the accelerometer near said proximal end of said elongated flexible member;
disposing the flex sensor in said elongated flexible member that is extending from near said proximal end to the near said distal end of the elongated flexible member;
providing a processing unit, said processing unit in electrical communication with said inertial sensor, said accelerometer and said flex sensor for receiving and processing data generated from one or more of inertial sensor, said accelerometer and said flex sensor;
receiving said processed data by a transmitting unit in electrical communication with processing unit;
transmitting said received data by said transmitting unit to an external computing device;
analyzing said received data by said external computing device; and
reporting of said illegal bowling action by said external computing device.

* * * * *